United States Patent [19]

Shoher et al.

[11] Patent Number: 4,797,100
[45] Date of Patent: Jan. 10, 1989

[54] METAL FOIL FOR FORMING A DENTAL COPING

[76] Inventors: Itzhak Shoher, 50 Shlomo-Hamelech St., Tel-Aviv, Israel, 64386; Aharon E. Whiteman, 13 J. L. Perez St., Petach-Tikvah, Israel, 49206

[21] Appl. No.: 56,054

[22] Filed: Jun. 1, 1987

[51] Int. Cl.⁴ .............................................. A61C 5/08
[52] U.S. Cl. ................................. 433/222.1; 433/218
[58] Field of Search ............... 433/206, 207, 208, 218, 433/222.1, 223, 227

[56] References Cited

U.S. PATENT DOCUMENTS

| | | | |
|---|---|---|---|
| 305,238 | 9/1884 | Rynear | 433/218 |
| 1,712,043 | 5/1929 | Limbarth | 433/206 |
| 4,492,579 | 1/1985 | Shoher et al. | 433/218 |

Primary Examiner—Samuel Scott
Assistant Examiner—Noah Kamen
Attorney, Agent, or Firm—E. Lieberstein

[57] ABSTRACT

A metal foil for forming a dental coping in the construction of a dental restoration comprising at least two or more layers of precious metal with a disc-like shape and a cross-section of variable thickness and/or an undulating surface geometry.

10 Claims, 2 Drawing Sheets ated into a
METAL FOIL FOR FORMING A DENTAL COPING This invention relates to a metal foil for forming a dental coping in the preparation of a dental restoration.

BACKGROUND OF INVENTION

A metal coping is used in dentistry in the construction of a dental crown and bridge. The metal coping functions as the understructure of the crown and is usually covered with a fired on coating of a ceramic or acrylic composition for purposes of aesthetics. The metal coping supports the coating and provides the structural strength and rigidity for the restored tooth to resist the force of mastication.

A metal coping has recently been developed for constructing a porcelain to metal crown which can be formed without waxing, investing or casting. The coping is described in U.S. Pat. Nos. 4,459,112 and 4,492,579 and consists of a thin metal foil of two or more layers of metal having a prefabricated geometry with a plurality of foldable sections. The foldable sections are folded over when the foil is adapted to the die so that they overlap. The unfolded metal foil is very thin, generally between about only 15 to 100 microns in thickness which permits the foil to the readily adapted to the die. However, once the foldable sections are folded over, the foil thickness is increased by the number of folded over layers of metal.

After the coping is adapted to the die, it is heat treated which sinters the overlapping folds one another forming a unitary mass. The coping, in its final form, possesses substantially increased strength and rigidity relative to the unfolded metal foil.

The amount of force which the coping must endure to maintain the integrity of the restoration depends upon the tooth to be restored which in turn depends upon the location of the tooth in the mouth. Posterior teeth, particularly molars, need to be much stronger than anterior teeth and accordingly require a stronger coping. The metal foil of the present invention will form a coping of substantial strength and resistance to fracture.

SUMMARY OF THE INVENTION

In one embodiment of the present invention, the metal foil for forming a dental coping comprises at least two layers of metal in a circular disk like shape having a cross section of variable thickness over at least a portion thereof.

In another embodiment of the present invention, the metal foil for forming a dental coping comprises at least two layers of metal having a disk like shape and an undulating surface geometry surrounding an area in the center of the disk.

The first embodiment may be combined with the second embodiment such that the metal foil has an undulating surface geometry about an annular area surrounding an area in the center of the foil with the annular area having a cross section with a variable thickness.

OBJECTS AND BRIEF DESCRIPTION OF THE DRAWINGS

Accordingly, it is the principal object of the present invention to provide a metal foil for forming a dental coping, particularly for a posterior dental restoration, which has a reinforced occlusal surface highly resistant to fracture.

It is a further object of the present invention to provide a metal foil for forming a dental coping having an undulating surface geometry adapted to form a multiple number of foldable sections which will overlap around the circumference of a posterior tooth. These and other objects of the present invention will become apparent from the following detailed description of the invention when read in conjunction with the accompanying drawing of which:

DETAILED DESCRIPTION OF THE INVENTION

Figure 1:
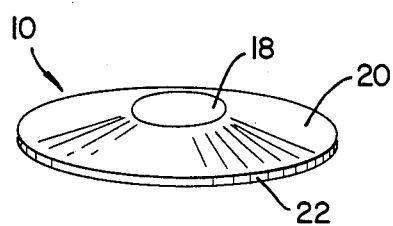
FIG. 1 is a perspective view of one embodiment of the metal foil of the present invention.
Figure 2:
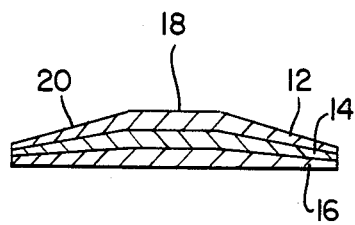
FIG. 2 is a cross section of the metal foil of FIG. 1 taken along the lines 2—2 in FIG. 1.

Referring now more particularly to the drawings in which the metal foil 10 of the present invention is shown composed of two or more layers of metal preferably in a laminated arrangement and machined into a generally circular disk like shape. The number of layers is not critical to the invention although at least three layers of metal as is shown in FIG. 2 is preferred.

The intermediate layer 12 of the metal foil 10 is formed of a high fusing temperature precious metal or metal alloy composed of, e.g., palladium or platinum or a combination thereof, each alone or in combination with other metals or metal alloys. A high fusing temperature metal for purposes of the present invention is intended to mean a metal having a melting temperature of above about 1250° C. The layers 14 and 16 which are located on opposite sides of layer 12, should preferably also be composed of a precious metal or metal alloy having a low fusing temperature relative to the high fusing temperature precious metal layer 12. The preferred low fusing metal layer is of gold or a gold alloy. Although only three layers are shown, any desired number of layers may be used and preferably with each metal layer of high fusing temperature having two symmetrically disposed layers of low fusing temperature on opposite sides thereto. In a two layer arrangement only a high and low fusing metal is required.

The disk like metal foil 10 has a central region 18 and a surrounding annular region 20. The annular region 20 is of a variable thickness which tapers downwardly and preferably linearly to the periphery 21 of the foil 10. The central region 18 is intended to be mounted over the occlusal surface of the restoration and accordingly should be thicker than the surrounding annular region 20 to reinforce the occlusal surface area without substantially affecting the ability to adapt the foil to a die. For a posterior molar the central region 18 should have a thickness in a range of from about 100 to 120 microns and a surrounding annular area 20 which gradually tapers down in thickness to about 50 microns at the periphery 21. For a premolar or canine restoration, the central region 18 should have a thickness in a range of from 80 to 100 with the surrounding area 20 tapering gradually downwardly to about 50 microns in thickness at the periphery 21. For an anterior restoration the central region 18 should have a thickness in a range of from 60 to 80 microns with the surrounding area 20 tapering gradually downwardly to about 50 microns in thickness at the periphery 21.

Figure 5:
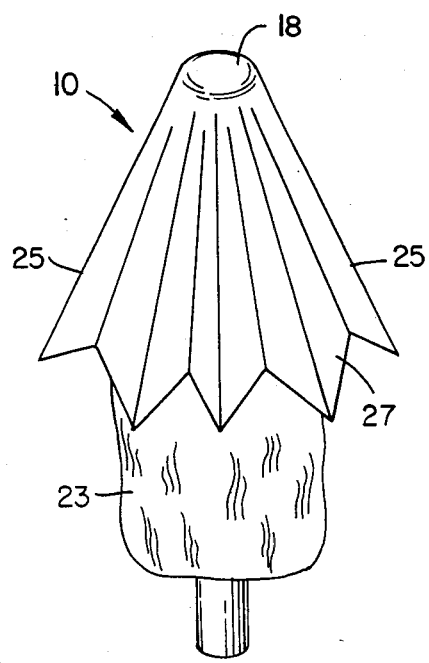
FIG. 5 is a perspective of the metal foil of the present invention shown in a prefolded arrangement mounted on a die of a tooth for forming a dental coping.
Figure 6:
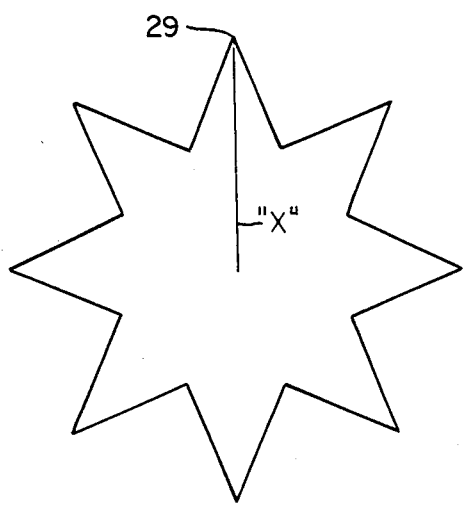
FIG. 6 is a view in elevation looking up from the bottom of the prefolded metal foil of FIG. 5 with the die removed.
Figure 7:
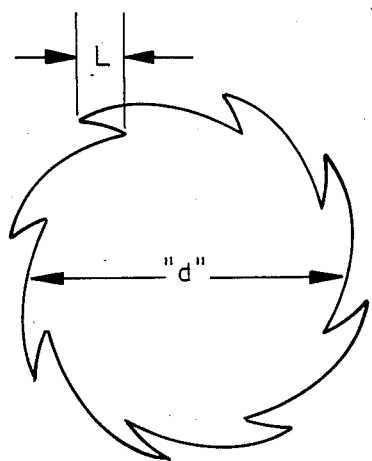
FIG. 7 shows the star like projections of FIG. 5 folded over each other prior to adapting the metal foil to the die.

Since a posterior tooth has a larger circumference than an anterior tooth, a coping for a posterior restoration should preferably have a larger surface area than a coping for an anterior restoration. However, the coping surface area cannot be increased simply by increasing the diameter of the metal foil since all excess material beyond the gingival margin is removed in the preparation of a restoration. This may be more readily understood from FIGS. 5-7. In FIG. 5 the metal foil 10 is shown in a prefabricated prefolded configuration mounted upon a die 23 of a tooth before the foil is adapted to the die. The foil is adapted to the die either by hand or by swaging using a conventional swaging device. The metal foil 10 is prefolded to form at least two foldable sections 25 although a multiple number is preferred. The prefolding operation for forming a coping is taught in U.S. Pat. Nos. 4,459,112 and 4,492,479. The foldable sections 25 provide added thickness of metal around the body of the die 23 before adapting the foil to the die. After the foil is adapted to the die and sintered, an acrylic or ceramic material is coated over the coping and fired. Before firing the final glaze, the area below the line 27, representing the gingival marging, is cut off. Accordingly, as shown in FIG. 7, the diameter "d" of the die 23 will control the distance "l" that each foldable section 25 for a given size foil overlaps an adjacent section. Since the diameter "d" of an anterior tooth is relatively small, the overlap distance "l" will, correspondingly, be large. Conversely, where "d" is large, as in a molar restoration, the overlap distance "l" will be small. The foldable sections 25 of the prefolded foil 10 form star-like projections in elevation, looking up from the bottom of the foil as shown in FIG. 6. The distance "x" representing the radial distance to the apex 29 between each foldable section 25 determines the degree of overlap "l" for a given size die. In accordance with the present invention, this distance "x" is varied to provide greater surface area without increasing the diameter of the metal foil.

Figure 3:
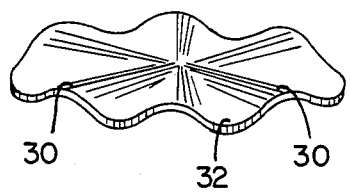
FIG. 3 is a perspective view of another embodiment of the metal foil of the present invention.
Figure 4:
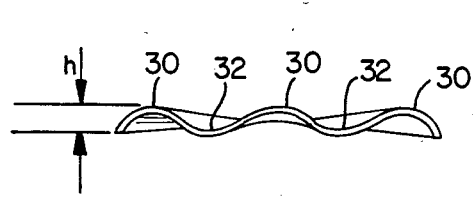
FIG. 4 is a cross sectional view of the metal foil of FIG. 3.

To increase the metal foil surface area sections of the metal foil are stretched to form an undulating surface as shown in FIG. 3. The undulating surface provides raised sections 30 which deviate a total distance "h" from a flat horizontal plane. The raised sections 30 may be formed by stretching the foil between adjacent sections 32 which are held relatively stationary. The stretched raised sections 30 will be thinner but provide the metal foil with a larger surface area. The distance "h" is controlled by how much the foil is stretched. This in turn controls the distance "x". Accordingly, for a posterior tooth such as a molar with a large circumference the metal foil should be stretched to produce undulation with larger excursions "h" than would be needed for a premolar or canine. Little or no stretching is needed for an anterior tooth.

We claim:

1. A metal foil for forming a dental coping in the construction of a ceramic or acrylic to metal dental restoration in which the coping represents the metal understructure of the dental restoration and is sized for adaptation to fit the tooth to be restored, comprising two or more layers of precious metal having a circular disk like shape with at least one layer of high fusing temperature metal and at least one layer of low fusing temperature metal and with said metal foil having a central area forming the occlusal surface of the coping and a cross section with a variable thickness extending from the central area to the periphery of the foil.

2. A metal foil as defined in claim 1 wherein said variable thickness tapers down gradually to the periphery of the foil.

3. A metal foil as defined in claim 2 wherein said region of variable thickness has an undulating surface geometry.

4. A metal foil as defined in claims 2 or 3 wherein said central area is substantially thicker than the thickness at the periphery.

5. A metal foil as defined in claim 4 for use in preparing a posterior molar wherein said central area has a thickness in a range of from about 100 to 120 microns.

6. A metal starting material as defined in claim 4 wherein said foil tapers gradually from said central area to a thickness of about 50 microns.

7. A metal starting material as defined in claim 4 for use in preparing a premolar or canine restoration wherein said central area has a thickness in a range of from about 80 to 100 microns.

8. A metal starting material as defined in claim 4 for use in preparing an anterior restoration wherein said central area has a thickness in a range of from about 60 to 80 microns.

9. A metal foil for forming a dental coping in the construction of a ceramic or acrylic to metal dental restoration in which the coping represents the metal understructure of the dental restoration and is sized for adaptation to fit the tooth to be restored comprising two or more layers of precious metal having a circular disk like shape with at least one layer of high fusing temperature metal and at least one layer of low fusing temperature metal and an undulating surface geometry surrounding an area in the center of the disk where the circumference undulates about its perimeter.

10. A metal foil as defined in claim 9 wherein said undulating area forms raised sections which have been stretched to increase the surface area of said foil.

* * * * *